United States Patent [19]

Domergue et al.

[11] 4,060,531
[45] Nov. 29, 1977

[54] COUMARIN DERIVATIVES

[75] Inventors: Annick Marthe Suzanne Simone Domergue, Eaubonne; Robert Frédéric Michel Sureau, Enghien les Bains, both of France

[73] Assignee: Produits Chimiques Ugine Kuhlmann, Paris, France

[21] Appl. No.: 682,294

[22] Filed: May 3, 1976

Related U.S. Application Data

[63] Continuation of Ser. No. 351,942, April 17, 1973, abandoned.

[30] Foreign Application Priority Data

Apr. 18, 1972  France .................... 72.13524

[51] Int. Cl.$^2$ ................ C07D 249/06; C07D 249/08
[52] U.S. Cl. .............. 260/308 R; 252/301.2; 252/9; 260/308 A
[58] Field of Search ............... 260/308 R, 308 A

[56] References Cited

U.S. PATENT DOCUMENTS

| | | | |
|---|---|---|---|
| 3,271,412 | 9/1966 | Raue et al. | 260/308 B |
| 3,288,804 | 11/1966 | Fleck et al. | 260/308 B |
| 3,658,833 | 4/1972 | Kabas et al. | 260/308 A |

OTHER PUBLICATIONS

Domergue et al., C.A. 80, 49275j (1974)-Abstract of Ger. Offen. No. 2,319,828 of 10-25-73.

*Primary Examiner*—Raymond V. Rush
*Attorney, Agent, or Firm*—Beveridge, DeGrandi, Kline & Lunsford

[57] ABSTRACT

Coumarin compounds of the formula:

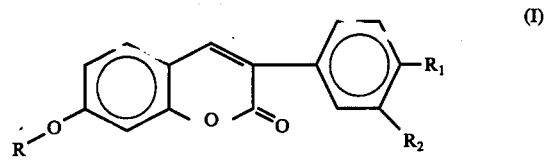

(I)

in which R represents an alkyl group containing 1 to 5 carbon atoms, either unsubstituted or substituted by a non-ionic and non-chromophoric group, one of the substituents $R_1$ or $R_2$ represents a triazole radical, and the other represents hydrogen or a halogen, or an alkyl group containing from 1 to 3 carbon atoms, the triazole radical being unsubstituted or substituted by one or two substituents consisting of an alkyl group containing from 1 to 3 carbon atoms or an aryl group; processes for their preparation and their use as fluorescent brightening agents for polyester fibres.

10 Claims, No Drawings

COUMARIN DERIVATIVES

This is a continuation of application Ser. No. 351,942, filed Apr. 17, 1973, now abandoned.

The invention relates to new coumarin derivatives, to their preparation and to their use and their application as fluorescent brightening agents for polyester fibres.

It has already been proposed to use as fluorescent brightening agents 7-alkoxy-coumarins substituted in the 3-position by a (2)-4-benzotriazolyl-phenyl radical (French Pat. No. 1,411,433). But in general these compounds give brightening agents verging on green on polyester fibres, and therefore are not much appreciated or not very efficient. They are only moderately fast to light.

It has now been found according to the present invention that it is possible to obtain on fibres based on polyesters a much more neutral whitening effect having excellent general fastness.

By "polyester fibers" are meant the fibres obtained by polycondensation of diacids with dialcohols, especially those resulting from the polycondensation of terephthalic acid with ethyleneglycol. Such fibres are sold on the market by the names of "Tergal", "Dacron", and "Terylene".

The compounds enabling an improvement of the whitening effect to be obtained correspond to the general formula:

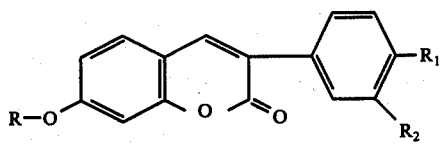

(I)

in which R represents an alkyl group containing 1 to 5 carbon atoms possibly substituted by a non-ionic and non-chromophoric group, one of the substituents $R_1$ or $R_2$ represents a triazole radical, the other represents a hydrogen or halogen atom or an alkyl group containing from 1 to 3 carbon atoms, the triazole radical possibly carrying one or two substituents consisting of an alkyl group containing from 1 to 3 carbon atoms or an aryl group.

The triazole radical, for example, may carry two substituents which may be the same or different.

The aryl group is a benzene radical possibly carrying from one to three substituents consisting, for example, of a halogen atom or an alkyl group containing 1 to 3 carbon atoms.

In the new compounds, the triazole radical may have the 1,2,4 structure and be preferably linked to the phenyl radical at the 1 position.

It may also have the 1,2,3 structure, and be linked preferably at one of its 4 or 2 positions to the phenyl radical.

The non-ionic and non-chromophoric groups, for example, may be a halogen or a hydroxy, methoxy or ethoxy group.

These new fluorescent brightening agents may be obtained for example by various processes known for the synthesis of coumarins such as:

1. Reaction of a diazonium salt of formula (II) with a coumarin of formula (III)

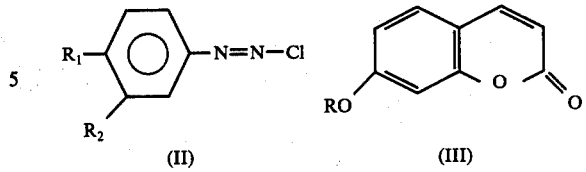

in which formulae R, $R_1$ and $R_2$ have the same significance as above.

2. Reaction of an orthohydroxy-benzaldehyde of formula (IV) with an acid of formula (V) or one of its functional derivatives:

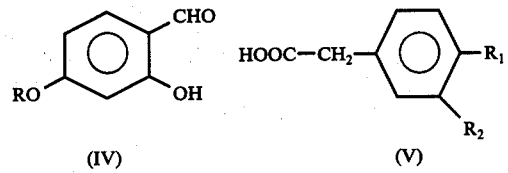

in which formulae R, $R_1$, and $R_2$ have the same significance as above. The functional derivatives of the acid (V) may be, for example, an alkali metal salt, the nitrile, or a methyl or ethyl ester.

3. Alkylation of a compound of the formula:

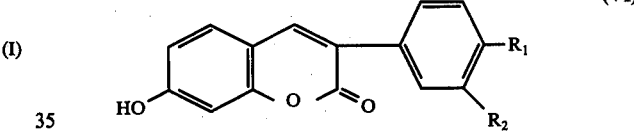

(VI)

in which $R_1$ and $R_2$ have the same significance as above, by means of an alkylating agent for example a dialkyl sulphate, such as dimethyl or diethyl sulphate.

The compound of formula (VI) may itself be prepared for example by one of the following methods:

reaction of the diazonium salt of formula (II) with 7-hydroxy-coumarin, or reaction of the acid of formula (V) or one of its functional derivatives with 2,4-dihydroxybenzaldehyde.

The functional derivatives of the acid (V) may comprise, for example an alkali metal salt, the nitrile or the methyl or ethyl ester.

The compounds according to the invention are light yellow or nearly white powders, insoluble in water, soluble in organic media such as for example alcohols, dioxan, or aromatic hydrocarbons, in which they show a very bright violet-blue fluorescence.

In order to brighten the organic fibrous materials, especially polyester fibres, the compounds of the invention are used in the form of aqueous dispersions. The concentration of brightening agent may vary for example from 0.005% to 0.5% with regard to the weight of the fibrous material. The blueing or brightening may be effected by dyeing under pressure, for example at between 120° C and 130° C or at the boil at ordinary pressure in the presence of an agent which makes the fibre swell ("carrier"). The fibres brightened with the coumarins according to the invention show a dazzling brightening effect in daylight, as well as excellent general fastness, especially to light.

The following Examples illustrate the present invention, without restricting the scope thereto. The parts and percentages are by weight.

EXAMPLE 1

Preparation of 3-[4-(3,5-dimethyl-1,2,4-triazole-1-yl)-3-chloro-phenyl]-7-methoxy-coumarin 11.15 parts of (4-amino-2-chloro)-phenyl-3,5-dimethyl1,2,4-triazole are dissolved in 50 parts of water and 12.5 parts of concentrated hydrochloric acid. The mixture is cooled to 0° C and diazotised with a solution of 3.5 parts of sodium nitrite in 10 parts of water. This solution of the diazonium salt is added with stirring to a solution of 8.8 parts of 7-methoxy-coumarin in 50 parts of acetone containing 10 parts of sodium acetate. 1.25 parts of cuprous chloride in solution in 5 parts of water are immediately added and stirring is continued for 3 hours until gas ceases to be evolved. The oil obtained by decantation is taken up in a little alcohol and filtered. The coumarin derivative obtained (2.6 parts) is then crystallised from ethanol. It melts at 219° C, and shows a strong violet blue fluorescence in alcoholic solution.

Analysis

| Calc. for $C_{20}H_{16}Cl\ N_3O_3$ | C: 62.9% | N: 11.0% | Cl: 9.30% |
|---|---|---|---|
| Found: | 62.8% | 10.9% | 9.27% |

The aminotriazole initially used is obtained by condensation of 2-chloro-4-nitro-phenylhydrazine and diacetamide, then reduction of the nitro group.

EXAMPLE 2

The process of Example 1 is followed, but 22 parts of (5-amino-2-chloro)-1-phenyl-3,5-dimethyl-1,2,4-triazole and 17.6 parts of 7-methoxy-coumarin are used, and 8 parts of 3-[3-(3,5-dimethyl-1,2,4-triazole-1-yl)-4-chloro-phenyl]-7-methoxy-coumarin melting at 210° C are obtained.

Analysis

| Calc. for $C_{20}H_{16}Cl\ N_3O_3$ | 62.9% | H: 4.19% | N: 11.0% |
|---|---|---|---|
| Found: | 62.6 | 4.29 | 11.0 |

The starting compound was obtained by nitration of 2'-chloro-1-phenyl-3,5-dimethyl-1,2,4-triazole, then reduction of the nitro group.

EXAMPLE 3

The process of Example 1 is followed, but 20 parts of 4'-amino-4-phenyl-2-methyl-1,2,3-triazole and 20 parts of 7-methoxy-coumarin are used, and 20 parts of 3-[4-(2-methyl-1,2,3-triazole-4-yl)-phenyl]-7-methoxy-coumarin melting at 231° C are obtained.

Analysis

| Calc,. for $C_{19}H_{15}N_3O_3$ | C%: 68.4 | N%: 12.6 |
|---|---|---|
| Found: | 68.0 | 12.7 |

EXAMPLE 4

5 parts of the $N_1$-oxide of 3-[4-(4,5-dimethyl-1,2,3-triazol-2-yl)-3-chloro-phenyl]-7-methoxy-coumarin are dissolved in 250 parts of ethanol, 10 parts of pulverised zinc are added, and the mixture is refluxed and 30 parts of concentrated hydrochloric acid are added in a period of 2 hours. The product is concentrated and the filtrate is diluted with water. The precipitate is filtered off, washed with water, then with ethanol. 1.3 parts of 3-[4-(4,5-dimethyl-1,2,3-triazole-2-yl)-3-chlorophenyl]-7-methoxy-coumarin melting at 170° C are obtained by crystallisation from acetone.

Analysis

| For $C_{20}H_{16}Cl\ N_3O_3$ | % C | % H | % N | % Cl |
|---|---|---|---|---|
| Calculated | 62.9 | 4.19 | 11.0 | 9.10 |
| Found | 62.9 | 4.44 | 10.8 | 9.20 |

The starting compound is obtained by the process of Example 1, starting from 22.5 parts of the $N_1$-oxide of 1'[2-(4-amino-2-chloro-phenyl)-4,5-dimethyl]-1,2,3-triazole and 17 parts of 7-methoxy-coumarin. 5 parts of the coumarin derivative of m.p. 191° C (ethanol) are thus obtained.

EXAMPLE 5

The process of Example 1 is followed, but 6.7 parts of 5-amino-2-chloro-2-phenyl-4,5-dimethyl-1,2,3-triazole and 5.3 parts of 7-methoxy-coumarin are used, 2.5 parts of 3-[3-(4,5-dimethyl-1,2,3-triazol-2-yl)-4-chloro-phenyl]-7-methoxy-coumarin of melting point 180° C (acetone) being obtained.

The amino-phenyl-triazole initially used is obtained by nitration of (2'-chloro-2-phenyl-4,5-dimethyl)-1,2,3-triazole followed by reduction.

EXAMPLE 6

0.005 parts of the coumarin derivative obtained in Example 1 are dispersed in 100 parts of water with 0.010 parts of dispersing agent, then 1.25 parts of polyester are tinted under pressure at 130° C for 1¼ hours. After rinsing and drying, the fibre thus treated shows a very neutral brightening effect and excellent general fastness.

We claim:

1. Coumarin compound of the formula:

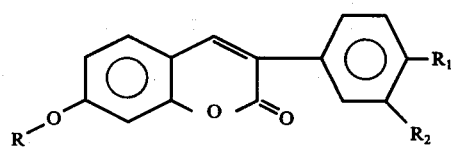

in which R represents an alkyl group containing 1 to 5 carbon atoms, one of the substituents $R_1$ or $R_2$ represents a triazole radical selected from the group consisting of 1,2,4-triazol-1-yl, 1,2,3-triazol-4-yl and 1,2,3-triazol-2-yl, and the other represents hydrogen or chlorine, or an alkyl group containing from 1 to 3 carbon atoms, the triazole radical being unsubstituted or substituted by one or two alkyl groups containing from 1 to 3 carbon atoms.

2. Compound according to claim 1 having the systematic name: 3-[4-(3,5-dimethyl-1,2,4-triazol-1-yl)-3-chlorophenyl]-7-methoxy-coumarin.

3. Compound according to claim 1 having the systematic name: 3-[3-(4,5-dimethyl-1,2,3-triazol-2-yl)-4-chlorophenyl]-7-methoxy-coumarin.

4. Compound according to claim 1 having the systematic name: 3-[3(3,5,dimethyl-1,2,4triazol-1-yl)-4-chlorophenyl]-7-methoxy-coumarin.

5. Compound according to claim 1 having the systematic name: 3-[4-(2-methyl-1,2,3-triazol-4-yl)-phenyl]-7-methoxy-coumarin.

6. Compound according to claim 1 having the systematic name: 3-[4-(4,5-dimethyl-1,2,3-triazol-2-yl)-3-chlorophenyl]-7-methoxy-coumarin.

7. Compounds according to claim 1 wherein the triazole radical has the 1,2, 4 structure.

8. Compounds according to claim 1 wherein the triazole radical has the 1, 2, 3 structure.

9. Compounds according to claim 8 wherein the triazole radical is linked to the phenyl radical by its 4 position.

10. Compounds according to claim 8 wherein the triazole radical is linked to the phenyl radical by its 2 position.

* * * * *